(12) United States Patent
Tyson

(10) Patent No.: US 12,383,332 B2
(45) Date of Patent: Aug. 12, 2025

(54) USER INTERFACE WITH DUAL-FUNCTION CONTROL SURFACE FOR POSITIONING MULTIPLE COMPONENTS WITHIN A BODY

(71) Applicant: Gyrus ACMI Inc., Westborough, MA (US)

(72) Inventor: Taylor N. Tyson, Seattle, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 817 days.

(21) Appl. No.: 17/554,031

(22) Filed: Dec. 17, 2021

(65) Prior Publication Data

US 2022/0192744 A1 Jun. 23, 2022

Related U.S. Application Data

(60) Provisional application No. 63/127,314, filed on Dec. 18, 2020.

(51) Int. Cl.
*A61B 18/14* (2006.01)
*A61B 18/00* (2006.01)
*A61B 18/12* (2006.01)

(52) U.S. Cl.
CPC ...... *A61B 18/1492* (2013.01); *A61B 18/1206* (2013.01); *A61B 2018/00577* (2013.01); *A61B 2018/00702* (2013.01)

(58) Field of Classification Search
CPC ............ A61B 18/1492; A61B 18/1206; A61B 2018/00577; A61B 2018/00702
See application file for complete search history.

(56) References Cited

U.S. PATENT DOCUMENTS

2021/0169564 A1* 6/2021 Desmarais ......... A61B 18/1477

* cited by examiner

*Primary Examiner* — Linda C Dvorak
*Assistant Examiner* — Abigail Bock
(74) *Attorney, Agent, or Firm* — Schwegman Lundberg & Woessner, P.A.

(57) ABSTRACT

Disclosed embodiments include apparatuses, systems, and methods for positioning electrodes using a single control surface. In an illustrative embodiment, an apparatus includes an actuator shaft defining a lumen through which a primary electrode and a secondary electrode are linearly movable. A primary actuator is movably couplable with the actuator shaft and a primary electrode with the primary actuator being configured to extend and retract the primary electrode. A secondary actuator is movably couplable with the primary actuator and a secondary electrode with the secondary actuator being configured to extend and retract the secondary electrode. An actuator controller is configured to move along the shaft in a first direction to engage and motivate the primary actuator and is further configured to move along the shaft in a second direction to engage and motivate the secondary actuator. The primary actuator and the secondary actuator are sequentially manipulatable using only the actuator controller.

11 Claims, 10 Drawing Sheets

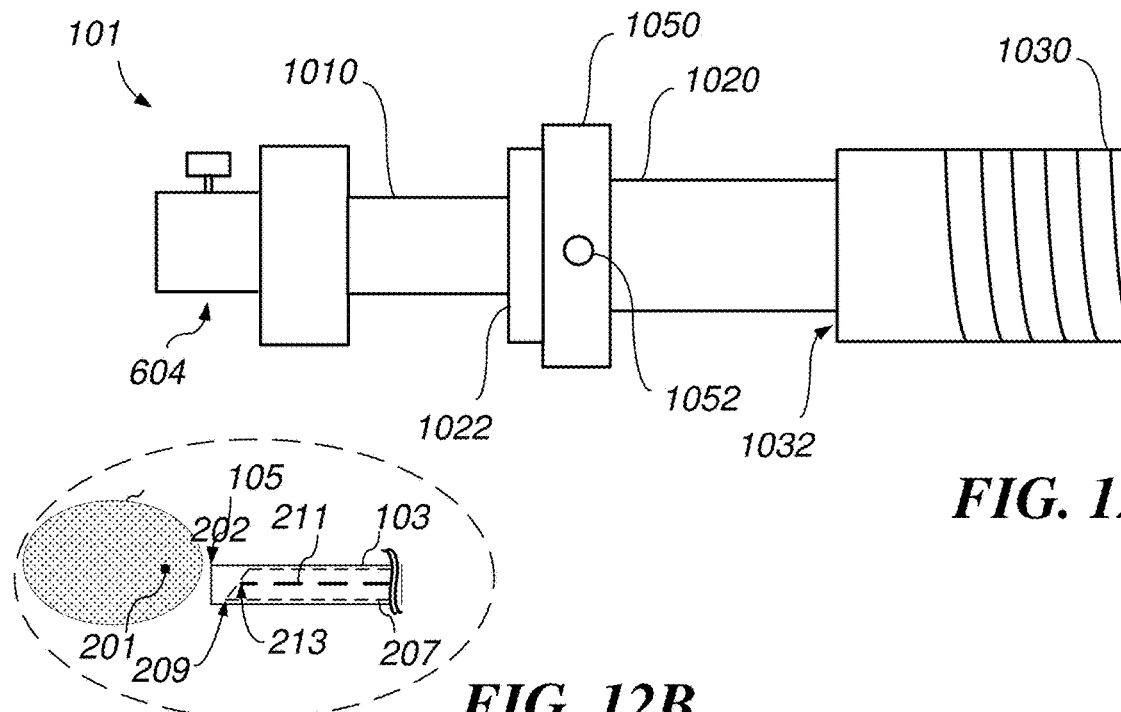
FIG. 12A
FIG. 12B
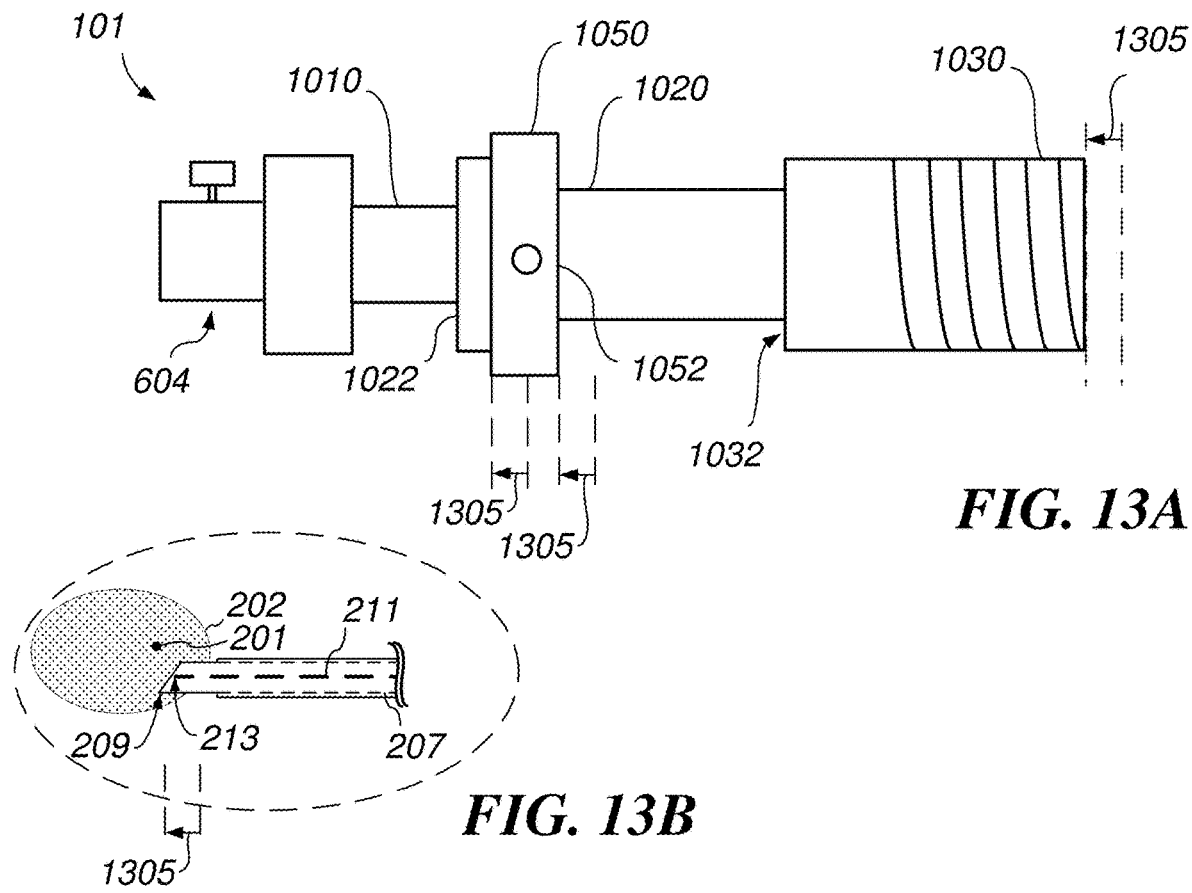
FIG. 13A
FIG. 13B

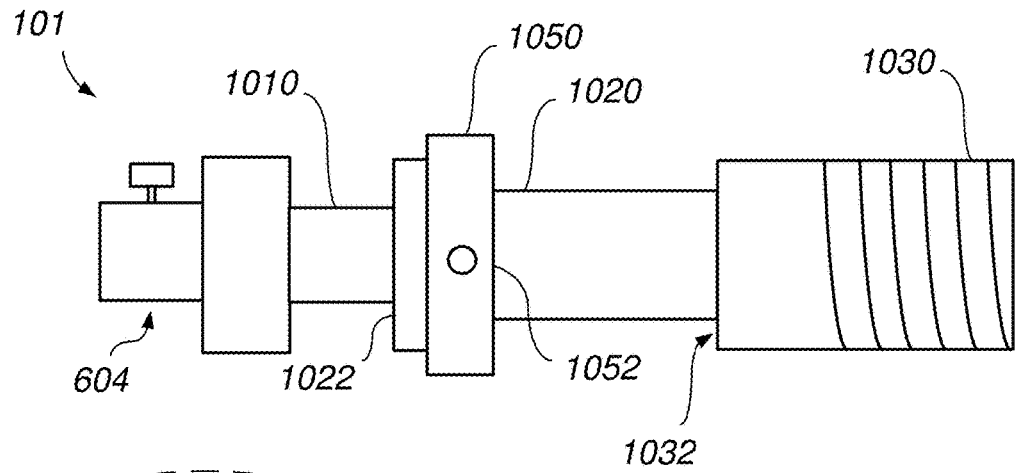
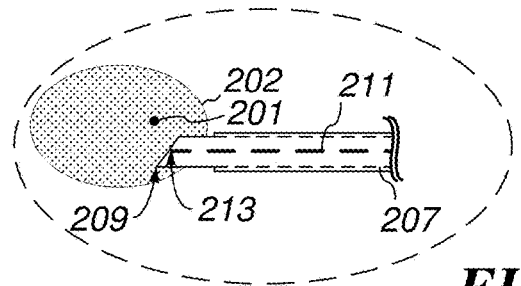
FIG. 16A
FIG. 16B
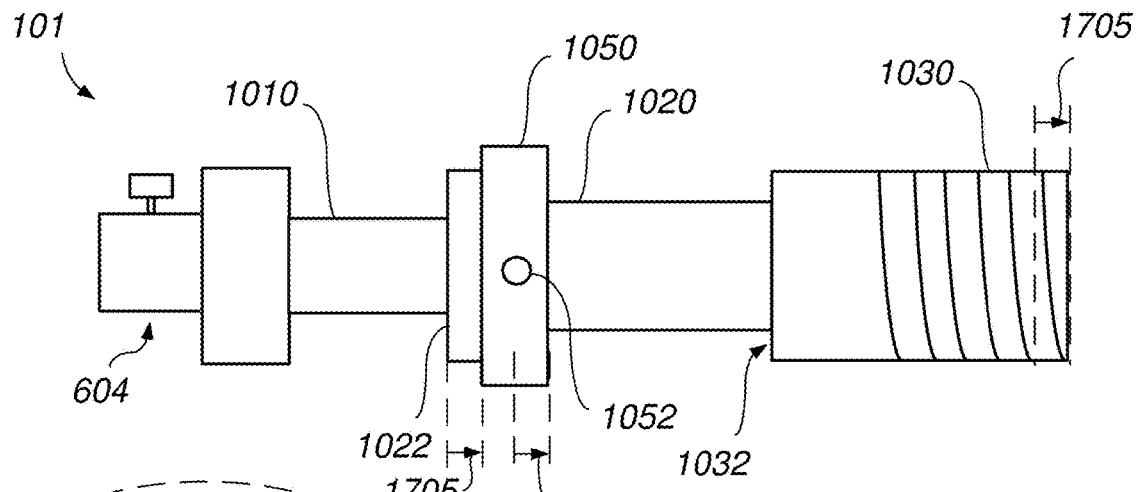
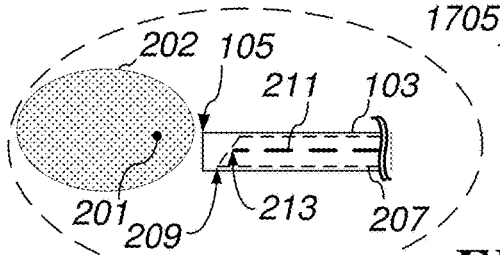
FIG. 17A
FIG. 17B

USER INTERFACE WITH DUAL-FUNCTION CONTROL SURFACE FOR POSITIONING MULTIPLE COMPONENTS WITHIN A BODY

PRIORITY CLAIM

This application claims the benefit of U.S. Provisional Application No. 63/127,314 file Dec. 18, 2020, the contents of which are hereby incorporated by reference.

FIELD

The present disclosure relates to a user interface and lock features for positioning multiple components within a body.

BACKGROUND

The statements in this section merely provide background information related to the present disclosure and may not constitute prior art.

Inserting and manipulating thin elements within living bodies or other objects allows for ever-improving types of analysis, diagnosis, and treatment of those bodies or objects with minimally invasive techniques. By way of two examples, endoscopic imaging and catherization treatments have enabled evaluation and treatment of numerous internal lesions without invasive surgery.

Electrosurgical techniques also provide for minimally invasive therapies by selectively applying electrical current to selected tissues. Electrosurgical techniques involve extending one or more electrodes through an orifice or a small incision to a desired location within a body, then applying a radio frequency ("RF") electric current to the electrodes to coagulate and/or ablate tissue at that location. Monopolar electrosurgical instruments only entail use of one electrode that interacts with a neutral electrode, which is likewise connected to the body of a patient. A bipolar electrosurgical instrument typically includes a user interface used for positioning two electrodes, which may include a distal electrode and a proximal electrode.

Positioning one or two electrodes at the desired location is an important part of such electrosurgical treatments. Moving and holding electrodes in place, particularly when more than one electrode has to be moved or held independently of another electrode, may present a challenge for medical personnel directing the treatment. Moreover, because a successful procedure may demand that a particular series of steps be followed in positioning each of the electrodes, simplifying control of the electrodes to assist an operator in placing the electrodes may be important.

SUMMARY

Disclosed embodiments include apparatuses for moving multiple components within a body with a single control surface for treating tissue at a reference point and methods for moving electrodes into positions for ablative electrical treatment at a reference point using a single control surface.

In an illustrative embodiment, an apparatus includes an actuator shaft defining a lumen through which a primary electrode and a secondary electrode are linearly movable along an axis of the lumen. A primary actuator is movably couplable with the actuator shaft and couplable with a primary electrode with the primary actuator being configured to extend and retract the primary electrode. A secondary actuator is movably couplable with the primary actuator and couplable with a secondary electrode with the secondary actuator being configured to extend and retract the secondary electrode. An actuator controller is configured to move along the shaft in a first direction to engage and motivate the primary actuator and is further configured to move along the shaft in a second direction to engage and motivate the secondary actuator. The primary actuator and the secondary actuator are sequentially manipulatable responsive to manipulation of only the actuator controller.

In another illustrative embodiment, a system for treating tissue at a reference point includes a controllable electrical power source configured to selectively provide electrical power between a first pole and a second pole. An electrosurgical apparatus is configured to be inserted into a body to convey a sheath housing a primary electrode electrically coupled with the first pole of the electrical power source and a secondary electrode electrically coupled with the second pole of the electrical power source to a vicinity of a reference point. A user interface includes an actuator shaft defining a lumen through which a primary electrode and a secondary electrode are linearly movable along an axis of the lumen. A primary actuator is movably couplable with the actuator shaft and couplable with a primary electrode with the primary actuator being configured to extend and retract the primary electrode. A secondary actuator is movably couplable with the primary actuator and couplable with a secondary electrode with the secondary actuator being configured to extend and retract the secondary electrode. An actuator controller is configured to move along the shaft in a first direction to engage and motivate the primary actuator and is further configured to move along the shaft in a second direction to engage and motivate the secondary actuator. The primary actuator and the secondary actuator are sequentially manipulatable responsive to manipulation of only the actuator controller.

In a further illustrative embodiment, a method includes positioning a user interface that includes a primary actuator operably coupled with a primary electrode and a secondary actuator operably coupled with a secondary electrode to position distal ends of the primary electrode and the secondary electrode adjacent to a target region. An actuator controller is moved in a first direction to engage the primary actuator. The actuator controller is manipulated to advance the primary actuator to extend both the primary electrode and the secondary electrode. The actuator controller is moved in a second direction to engage the secondary actuator. The secondary actuator is manipulated to advance the secondary actuator to independently extend the secondary electrode beyond the primary electrode.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings.

Figure 18:
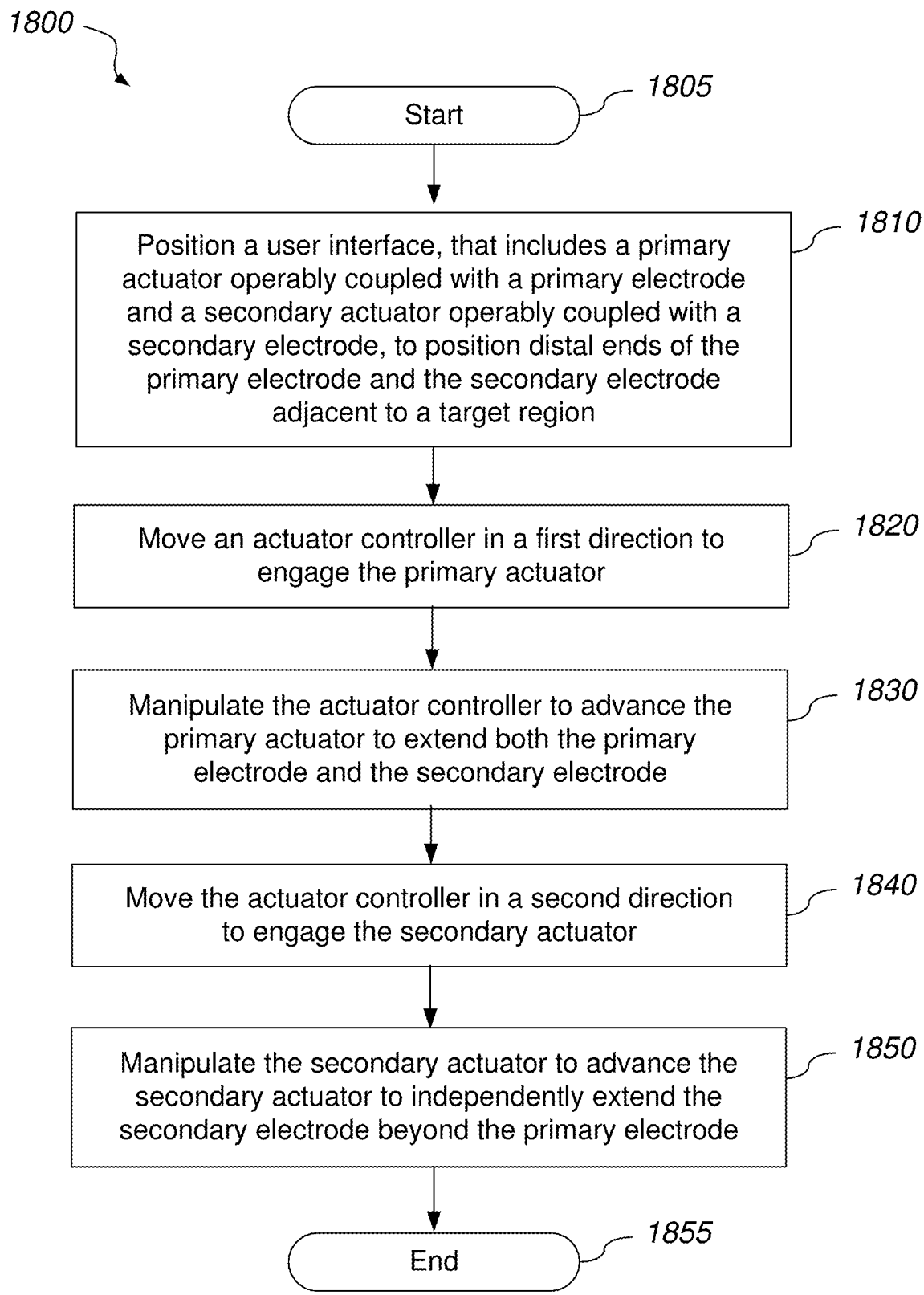

FIGS. 12A, 13A, 14A, 15A, 16A, and 17A are side views of an illustrative user interface for positioning multiple components relative to the reference point;

FIGS. 12B, 13B, 14B, 15B, 16B, and 17B are diagrams in partial schematic form of positioning of distal ends of a sheath, primary electrode, and secondary electrode relative to a reference point corresponding to positions of the components of the user interface of FIGS. 12A, 13A, 14A, 15A, 16A, and 17A, respectively; and FIG. 18 is a flow chart of an illustrative method of positioning components using a user interface.

DETAILED DESCRIPTION

The following description is merely illustrative in nature and is not intended to limit the present disclosure, application, or uses. It will be noted that the first digit of three-digit reference numbers, the first two digits of four-digit reference numbers correspond to the first digit of one-digit figure numbers and the first two-digits of the figure numbers, respectively, in which the element first appears.

The following description explains, by way of illustration only and not of limitation, various embodiments of user interfaces to position electrodes for electrosurgical apparatuses, as well as systems including such user interfaces and methods of using the same. As will be described in detail below, electrosurgical techniques position first and second electrodes adjacent a reference point where electrical treatment, such as ablative treatment, is to be applied. For a specific example, the user interfaces and methods of their use may be used for ablating and/or coagulating tissue, removing lesions, and for performing other medical procedures within the lung.

It will be appreciated that various embodiments of user interfaces described herein may help to simplify the process of positioning the electrodes and holding the electrodes in place. As will be described below, various embodiments of the user interface accomplish the selective positioning and locking in place of the electrodes by engaging, sliding, and/or rotating components.

Figure 1:
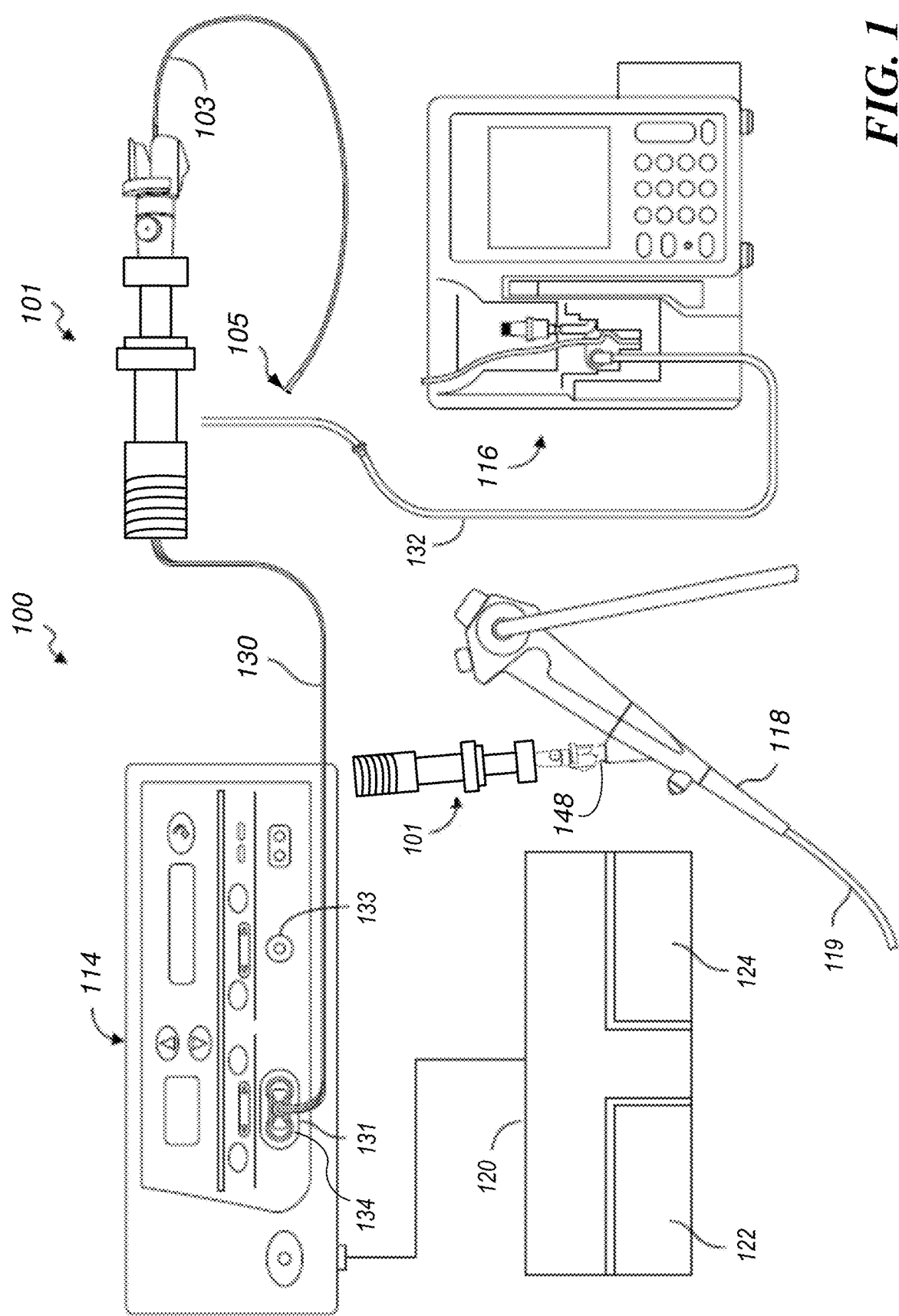
FIG. 1 is a block diagram in partial schematic form of an illustrative system for treating tissue.

Referring to FIG. 1, in various embodiments a system 100 is provided for treating tissue at a reference point in an anatomical region of a patient (not shown in FIG. 1). The system 100 may be a bipolar or monopolar radio frequency (RF) system, as desired, for treating tissue in a patient. Specifically, the system 100 may be employed for coagulation and/or ablation of soft tissue during percutaneous and/or endoscopic, including bronchoscopic, surgical procedures, such as, for example, partial and/or complete ablation of cancerous and/or noncancerous organ lesions. As will be further described, the tissue is treated by positioning one or more electrodes proximate the tissue to be treated and passing an electrical current through the tissue at a reference point.

In some embodiments, the system 100 includes a user interface 101, an electrosurgical radio frequency (RF) generator operating as a switchable current source 114, an infusion pump 116, and an electrosurgical instrument or apparatus, such as without limitation a bronchoscope 118. It will be appreciated that the electrosurgical instrument or apparatus may also include an endoscope or any other electrosurgical instrument as desired for a particular application. The bronchoscope 118 may be configured to receive the user interface 101 at a port 148 to enable the user interface 101 to manipulate electrodes at the reference point via the bronchoscope 118.

The user interface 101 electrically communicates with the switchable current source 114 though an electrical conductor 130. In some embodiments, the electrical conductor 130 is connected to an outlet 131 when the system is operated in a bipolar mode. The electrical conductor 130 may be coupled with the outlet 131 using an electrical connector 134 configured to electrically engage the outlet 131. In some other embodiments, the system 100 can be operated in a monopolar mode when the electrical conductor 130 is connected to a secondary outlet 133 with an adapter (not shown in FIG. 1) as desired. The user interface 101 is further connected to the infusion pump 116 with a tube 132 that facilitates the flow of liquid, for example saline solution, from the infusion pump 116 to the user interface 101.

The switchable current source 114 can be operated with the use of a foot operated unit 120 electrically connected to the switchable current source 114. The foot operated unit 120 includes a pedal 122 that instructs the switchable current source 114 to apply an electrical current to electrode(s) (described below) to cut and/or ablate tissue and a pedal 124 that instructs the generator 114 to apply a lower electrical current to the electrode(s) to coagulate tissue.

In various embodiments the bronchoscope 118 includes an insertion tube 119 that permits insertion of a sheath 103 into a body (not shown). A distal end 105 of the sheath 103 is delivered to a location near the tissue to be treated at the reference point. The sheath 103 contains and conveys the electrodes (not shown) to a desired treatment location. Positioning of the distal end 105 of the sheath 103 and the distal ends of the electrodes (not shown in FIG. 1) may be controlled by the user interface 101 received by the bronchoscope 118 at a port 148.

Referring additionally to FIGS. 2-5, in various embodiments distal ends of components are positioned relative to a reference point 201 using various embodiments of a user interface. The reference point 201, for example, may be at a point within a target region 202 such as a lesion or any portion of tissue to be treated within a body. Given by way of illustration only and not of limitation, the illustrative embodiments of the user interface described below all are capable of positioning the components as described with reference to FIGS. 2-5, as further described with reference to each of the described embodiments. The description of FIGS. 2-5 is provided as a baseline to describe the operation of the various embodiments of the user interface.

In various embodiments, a secondary electrode 211 is slidably received within a primary electrode 207, and the primary electrode 207 is slidably received within a sheath 103. In various embodiments, until a user interface is manipulated to separately move the primary electrode 207 and/or the secondary electrode 211, the primary electrode 207 and the secondary electrode 211 move in concert with the sheath 103, which means that the electrodes 207 and 211 move at a same time and through a same distance as the sheath 103. As will be described below, in some instances, the secondary electrode 211 also may move in concert with the primary electrode 209 while both electrodes move independently of the sheath 103. Components contained within other components are represented with dashed lines in FIGS. 2-5.

Figure 2:
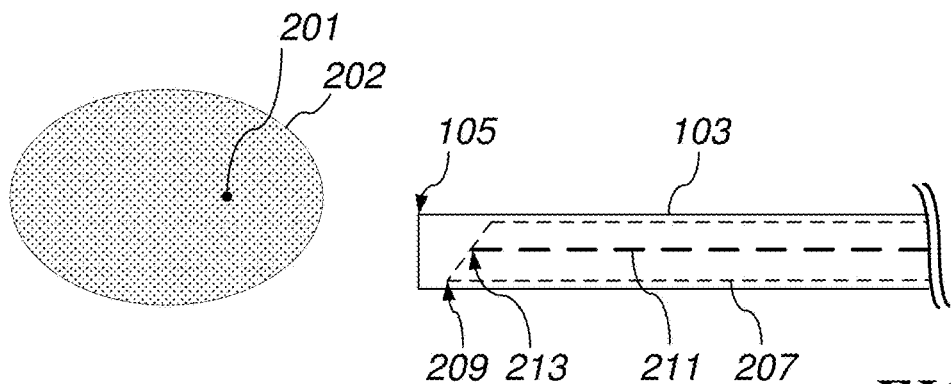
FIGS. 2-5 are diagrams in partial schematic form of positioning of distal ends of a sheath, primary electrode, and secondary electrode relative to a reference point.

As shown in FIG. 2, in various embodiments the sheath 103, the primary electrode 207, and the secondary electrode 211 are positioned at an initial position relative to the reference point 201 at or near the target region 202. More particularly, the components are positioned upon the insertion of the sheath 103 through an insertion tube in a bronchoscope, such as the insertion tube 119 and the bronchoscope 118 of FIG. 1, before they are moved into precisely desired locations by manipulating the user interface (not shown) as further described below.

In various embodiments a distal end 105 of the sheath 103 is positioned close to the target region 202. The primary electrode 207 is slidably received within the sheath 103, with a distal end 209 of the primary electrode 207 at or near the distal end 105 of the sheath 103. Specifically, FIG. 2, for example, shows the distal end 209 of the primary electrode 207 positioned just short of the distal end 105 of the sheath 103. In turn, the secondary electrode 211 is slidably received within the primary electrode 207, with the distal end 213 of the secondary electrode 211 positioned just within the distal end 209 of the primary electrode 207.

Figure 3:
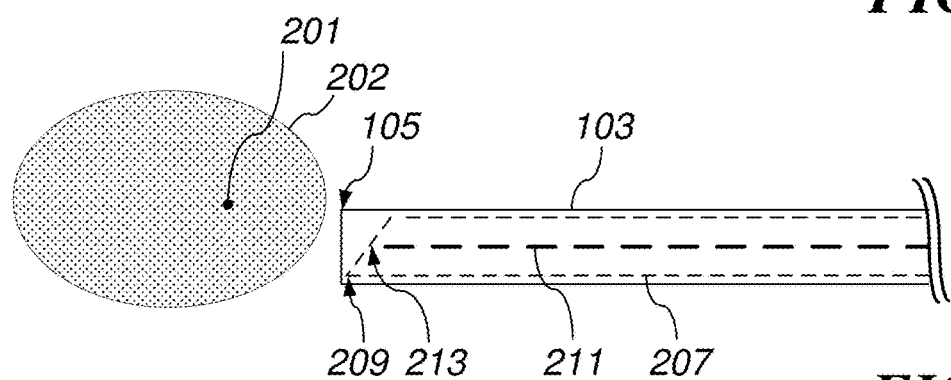

As shown in FIG. 3, in various embodiments the sheath 103, the primary electrode 207, and the secondary electrode 211 are positioned once the sheath 103 has been moved closer to the target region 202. As contrasted with FIG. 2, in FIG. 3 a distal end 105 of the sheath 103 has been moved closer to the reference point 201 at the edge of the target region 202. Just as in FIG. 2, because the primary electrode 207 and the secondary electrode 211 have not been separately moved through the manipulation of a user interface (not shown), the primary electrode 207 and the secondary electrode 211 have moved with the movement of the sheath 103. Thus, at the deployment position closer to the reference point 201, the distal end 209 of the primary electrode 207 remains positioned just short of the distal end 105 of the sheath 103. Similarly, the distal end 213 of the secondary electrode 211 remains positioned just within the distal end 209 of the primary electrode 207. As will be further described with reference to embodiments of a sheath lock that may be part of a user interface or used in conjunction with a user interface, once the distal end 105 of the sheath 103 has been moved to a desired location, the sheath 103 may be locked in place.

Figure 4:
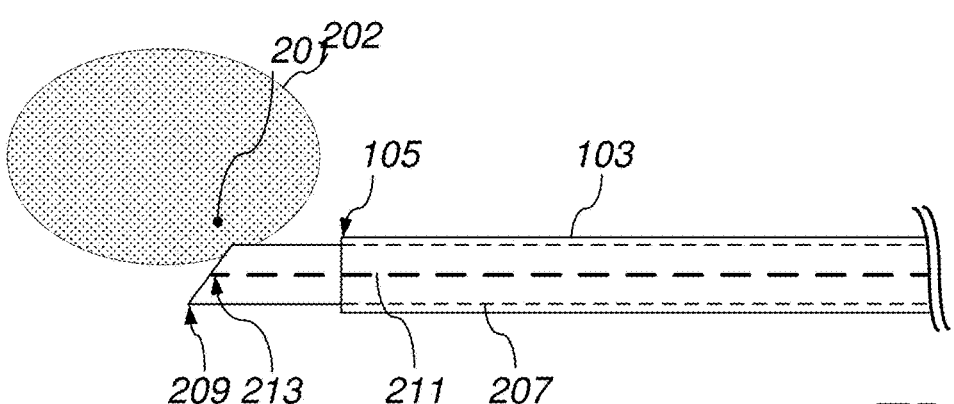

As shown in FIG. 4, in various embodiments the sheath 103, the primary electrode 207, and the secondary electrode 211 are positioned once the primary electrode 207 has been extended from the sheath 103 toward the reference point 201 and into the target region 202. In various embodiments, unless the user interface (not shown) is manipulated to disengage movement of the secondary electrode 211 from movement of the primary electrode 207, the secondary electrode 211 moves in concert with the primary electrode 207, with the secondary electrode 211 moving in the same direction and the same distance as the primary electrode 207. Thus, as shown in FIG. 4, the primary electrode 207 as the primary electrode 207 is extended beyond the distal end 105 of the sheath 103, and the secondary electrode 211 moves in concert with the primary electrode 207. As shown in FIG. 4, the distal end 209 of the primary electrode 207 is extended toward the reference point 201 and beyond the distal end 105 of the sheath 103. The distal end 213 of the secondary electrode 211 remains positioned just within the distal end 209 of the primary electrode 207. In various embodiments, the primary electrode 207 is in the form of a needle, with the distal end 209 being configured to pierce tissue, such as tissue comprising the target region 202, to enable the distal end 209 of the primary electrode 207 to reach a desired position, and to be able to situate the secondary electrode 211 at a desired point.

As will be further described below, once the distal end 105 of the sheath 103 is in a desired location and locked in place, embodiments of the user interface allow the primary electrode 207 to be unlocked so that the primary electrode 207 may be moved independently of the sheath 103. As also further described below, embodiments of the user interface may keep motion of the secondary electrode 211 locked with motion of the primary electrode 207 so that the distal end 213 of the secondary electrode 211 moves in concert with the distal end 209 of the primary electrode 207. As also further described below, embodiments of a user interface permit one or both of the primary electrode 207 and the secondary electrode 211 to be fixed in position—that is, remain in place—so that one or both of the electrodes 207 and 211 are secured at a current position. Thus, for example, a position of the primary electrode 207 may be fixed while the secondary electrode 211 may be moved independently of the primary electrode 207. Also, both electrodes 207 and 211 may be fixed in place, for example, when treatment is administered by applying an electrical current using an electrosurgical apparatus such as that shown in the system 100 of FIG. 1.

Figure 5:
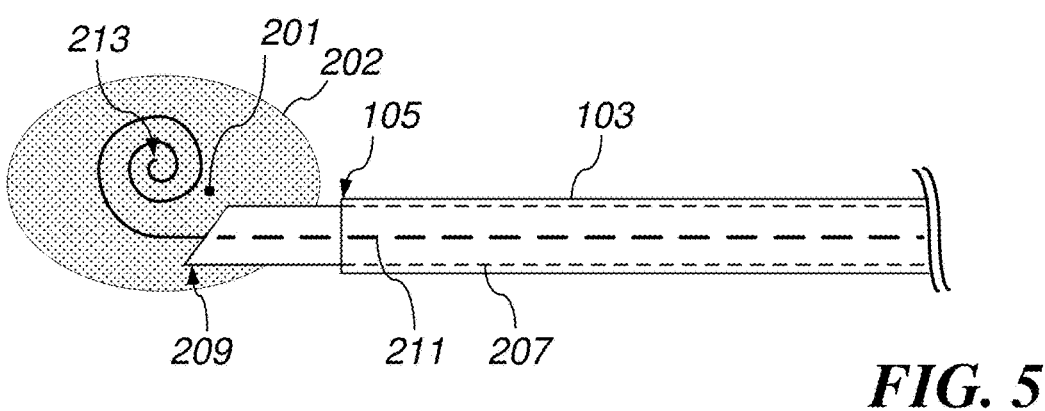

As shown in FIG. 5, in various embodiments the sheath 103, the primary electrode 207, and the secondary electrode 211 are positioned once the secondary electrode 211 has been extended from the primary electrode 207. A distal end 213 of the secondary electrode 211 is deployed at a position on an opposite side of the reference point 201 from the primary electrode 207. In various embodiments, the secondary electrode 211 is configured as coiled wire which is received within the primary electrode 207 in a straightened form. Once the user interface is manipulated to independently extend the secondary electrode 211 from the primary electrode 207, the secondary electrode 211 coils. As a result, the distal end 213 of the secondary electrode 211 corkscrews into tissue at the target region 202. The corkscrewing of the distal end 213 of the secondary electrode 211 may assist in securing the position of the distal end 213 of the secondary electrode 211 during treatment. Although not specifically shown in FIG. 5, a portion of the secondary electrode 211 may be coated with insulation, with the insulated portion stopping short of the distal end 213 of the secondary electrode 211. The insulation electrically insulates the secondary electrode 211 from the primary electrode 207 such that, when electrical current is applied to proximal ends (not shown) of the primary electrode 207 and the secondary electrode 211, the electrical current may only flow between the distal end 209 of the primary electrode 207 and the uninsulated distal end 213 of the secondary electrode 211.

Figure 6B:
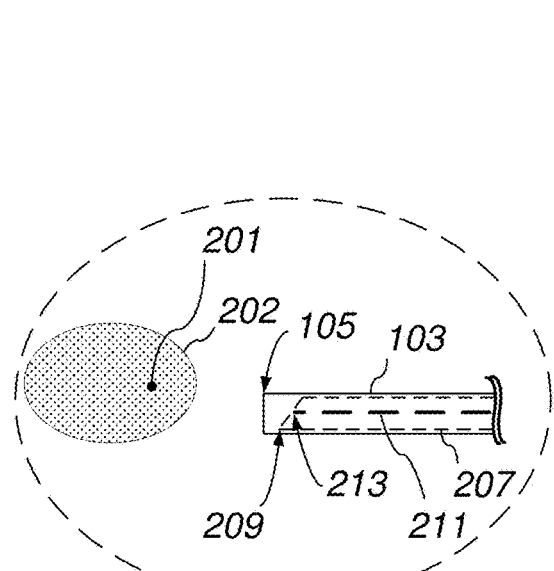
FIGS. 6B and 7B are diagrams in partial schematic form of positioning of distal ends of the sheath, a primary electrode, and a secondary electrode relative to a reference point corresponding to positions of the sheath actuator of FIGS. 6A and 7A, respectively.
Figure 6A:
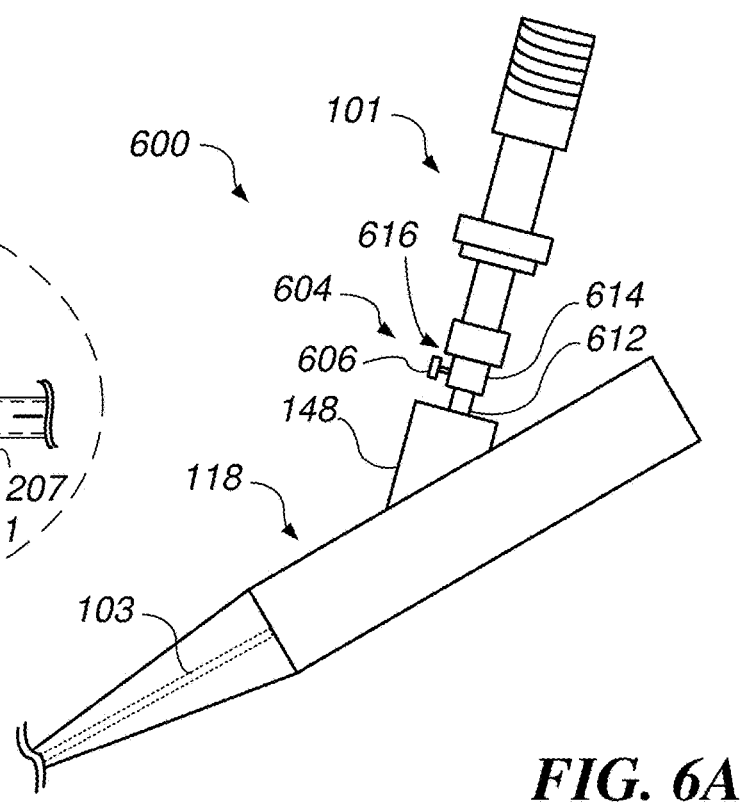
FIGS. 6A and 7A are diagrams in partial schematic form of an illustrative sheath actuator for positioning a sheath relative to a reference point.

Referring additionally to FIGS. 6A and 6B, in various embodiments an illustrative apparatus 600 includes an illustrative user interface 101 received at the port 148 of an electrosurgical apparatus 118, such as a bronchoscope or another minimally invasive device used for performing diagnostic or therapeutic tasks by extending a sheath or catheter into a body (not shown in FIGS. 6A and 6B). In various embodiments the user interface 101 includes a sheath actuator 604 and a sheath lock 606 configured to move the sheath 103 to a desired location to position a distal end 105 of the sheath 103 relative to the reference point 201. In some embodiments, the sheath actuator 604 may be a slidable mechanism that incorporates a slidable sleeve 612 that is received within a collar 614. The slidable sleeve 612 may be locked in position at the collar 614 by the sheath lock 606. The sheath lock 606 may be a spring-loaded locking pin, a thumbscrew, or another mechanism configured to mechanically engage the slidable sleeve 612 to secure the slidable sleeve 612—and, in turn, the sheath 103 (FIGS. 2-5)—in place at a desired location.

In some embodiments, the sheath actuator 604 may be part of the user interface 101. For example, in the user interface 101 of FIG. 6A, the slidable sleeve 612 is fixably engaged with the user interface 101 at a distal end 616 of the user interface 101. The collar 614 then may engage the port 148 on the electrosurgical apparatus 118, where movement of the slidable sleeve 612 within the collar 614 controls movement of the sheath 103 (FIGS. 2-5). In some other embodiments, the sheath actuator 604 may, for example, be part of the electrosurgical apparatus 118. The collar 614 may be fixably joined to the port 148. The slidable sleeve 612 may be associated with the port 148 to engage the distal end 616 of the user interface 101. In another embodiment, the slidable sleeve 612 may be fixably joined to the distal end 616 of the user interface 101 and be configured to receivably engage the collar 614 that is fixably attached to the port 148. Any of these embodiments of the sheath actuator 604 may facilitate movement of the sheath 103 as described below.

In various embodiments the user interface 101 is mechanically coupled with a primary electrode 207 that is slidably received within the sheath 103. In some such embodiments, a distal end 209 of the primary electrode 207 is positioned just short of the distal end 105 of the sheath 103. The user interface 101 is also mechanically coupled with a secondary electrode 211 slidably received within the primary electrode 207, with the distal end 213 of the secondary electrode 211 being positioned just within the distal end 209 of the primary electrode 207. It will be appreciated that various embodiments of the user interface 101 may be configured to secure the primary electrode 207 and the secondary electrode 211 relative to the sheath 103 so that both the primary electrode 207 and the secondary electrode 211 move in concert with the sheath 103 as the sheath is moved as described with reference to FIG. 3.

Figure 7B:
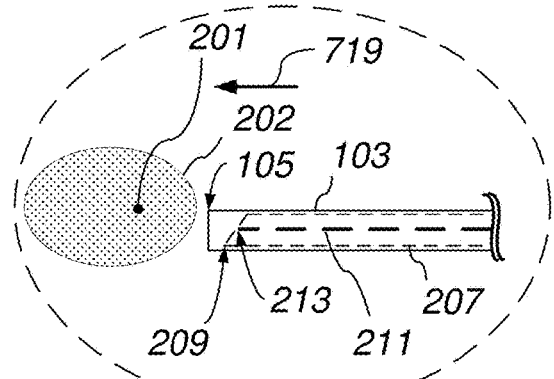
Figure 7A:
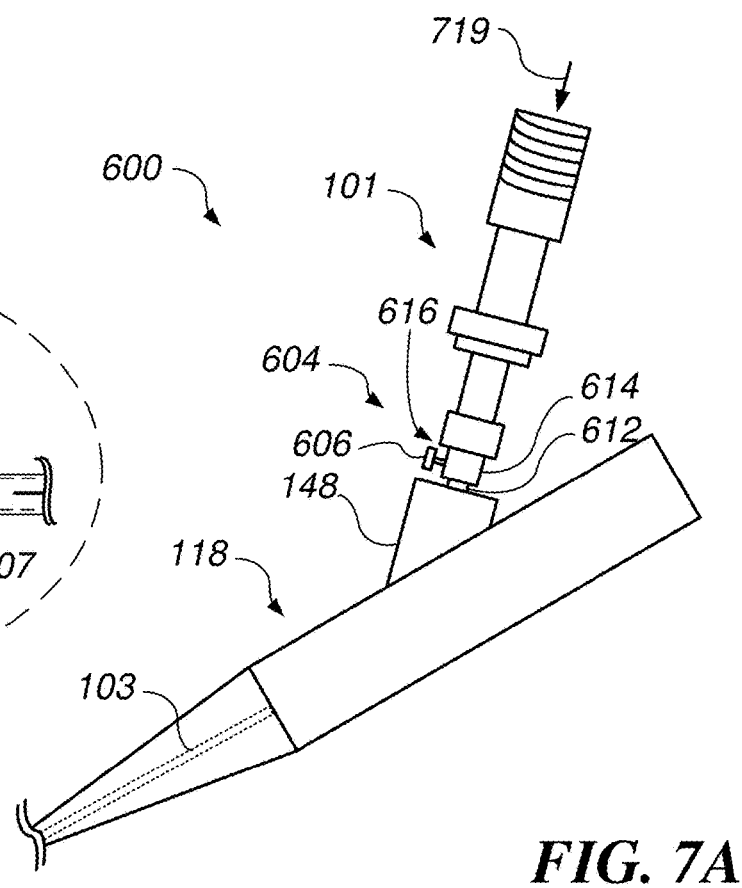

Referring additionally to FIGS. 7A and 7B, manipulation of the sheath actuator 604 illustrates an example of how the sheath 103 may be unlocked and moved into position as previously described with reference to FIG. 3. As shown in FIGS. 7A and 7B, the sheath actuator 604 has been manipulated to enable the sheath 103 to be moved a distance 719 closer to the reference point 201 and the target region 202. Specifically, once the sheath lock 606 of the sheath actuator 604 is manipulated to enable movement of the slidable sleeve 612 within the collar 614, the user interface 101 is moved the distance 719 to move the sheath 103 the same distance 719 toward the reference point 201 in the target region 202. Once the sheath 103 has reached the desired location, the slidable sleeve 612 may be locked in position at the collar 614 by the sheath lock 606. As will be described further below, in various embodiments, the user interface 101 maintains the positions of the primary electrode 207 and the secondary electrode 211 relative to the sheath 103 as the sheath actuator 604 is used to move the sheath 103. Therefore, a distal end 209 of the primary electrode 207 and a distal end 213 of the secondary electrode 211 also are moved by the distance 719 toward the reference point 201 in the target region 202.

Figure 8:
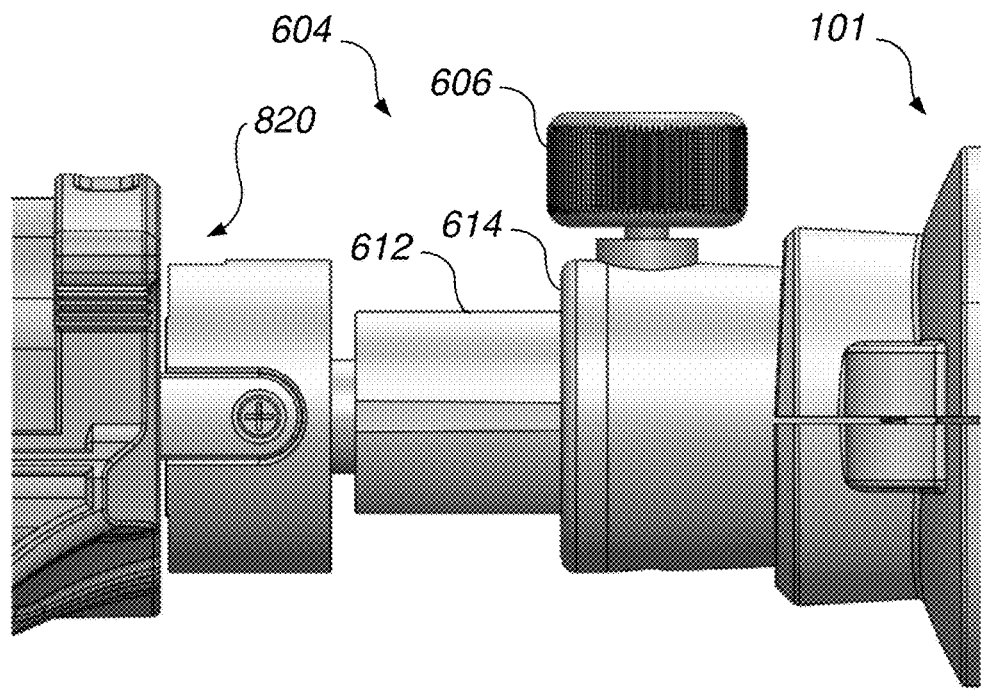
FIG. 8 is a side plan view of an illustrative sheath actuator and a sheath lock.

Referring additionally to FIG. 8, in various embodiments an illustrative sheath actuator 604 includes a slidable sleeve 612 that is fixably attached to a coupling 820 configured to engage a port (not shown in FIG. 8) of an electrosurgical apparatus (not shown in FIG. 8) such as a bronchoscope. In various embodiments, a sheath lock 606 may include, such as without limitation a thumbscrew or the like that that may be loosened to permit movement of a collar 614 that is fixably attached to the user interface 101 to move the sheath (not shown in FIG. 8) as previously described with reference to FIGS. 6 and 7. After the user interface 101 has been manipulated to slide the collar 614 relative to the slidable sleeve 612 to move the sheath to a desired location, the sheath lock 606 is re-engaged, such as by turning a thumbscrew, to fix the position of the sheath.

Figure 9:
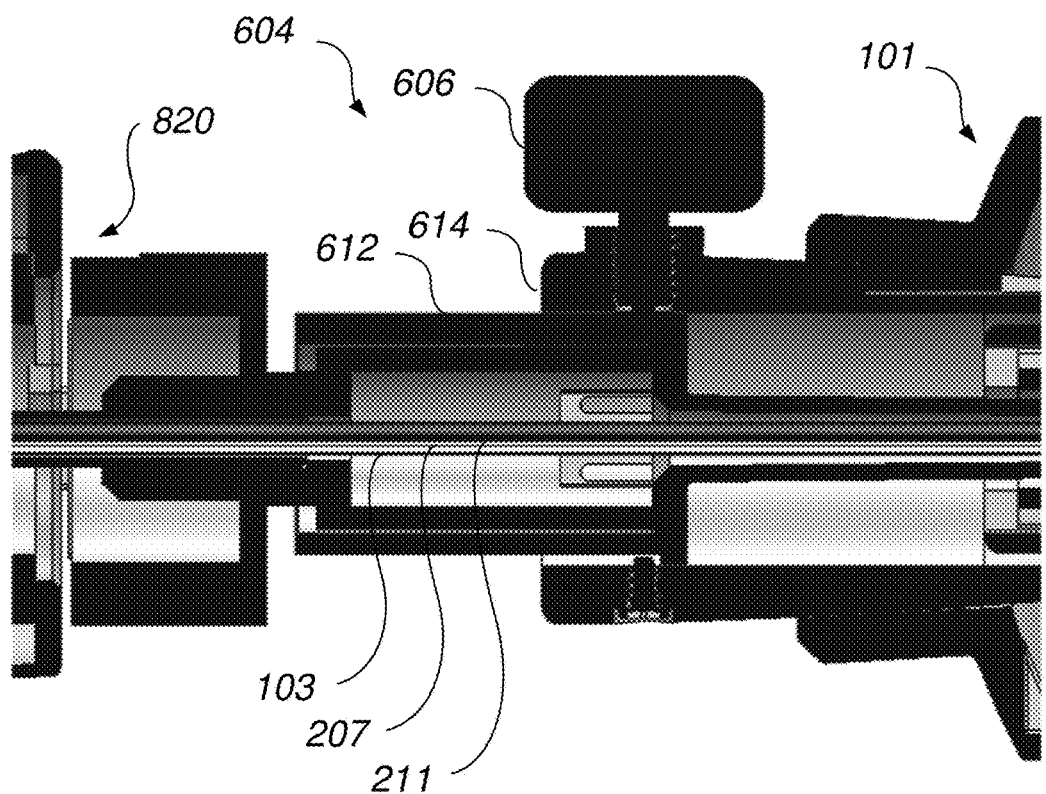
FIG. 9 is a side plan view in cutaway of the sheath actuator and sheath lock of FIG. 8.

Referring additionally to FIG. 9, in various embodiments the sheath actuator 604 includes the slidable sleeve 612 that is fixably attached to the coupling 820. In some embodiments the sheath lock 606 may include a thumbscrew that may be loosened to permit movement of the collar 614 that may be fixably attached to the user interface 101 to move the sheath 103 and, in concert therewith, the primary electrode 207 and the secondary electrode 211 received within the sheath 103. After the user interface 101 is manipulated to slide the collar 614 relative to the slidable sleeve 612 to move the sheath 103 to the desired location, the sheath lock 606 is turned to fix the position of the collar 614 relative to the slidable sleeve 612 to fix the position of the sheath 103.

Figure 10:
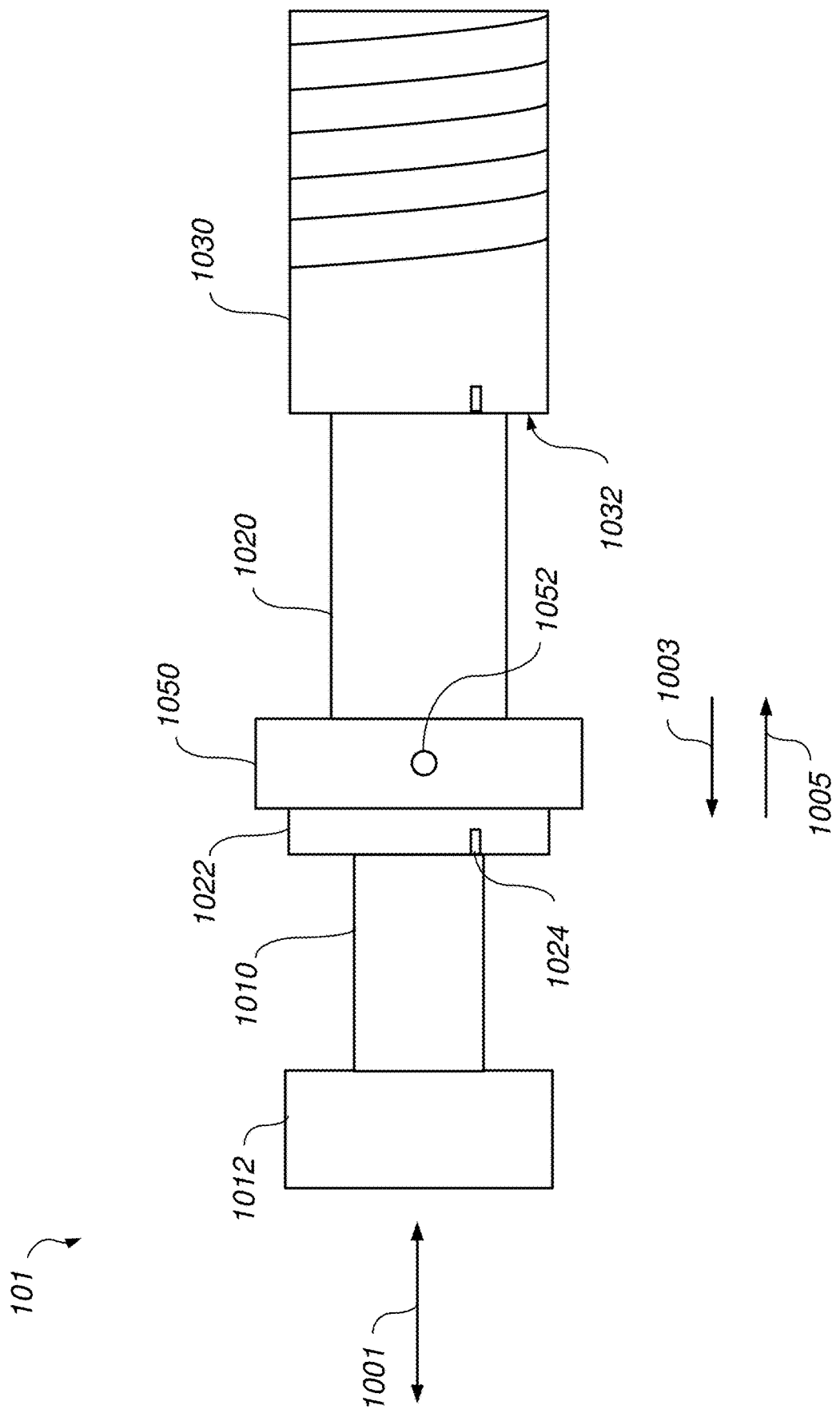
FIG. 10 is a side view of an illustrative user interface for positioning multiple components relative to the reference point.
Figure 11:
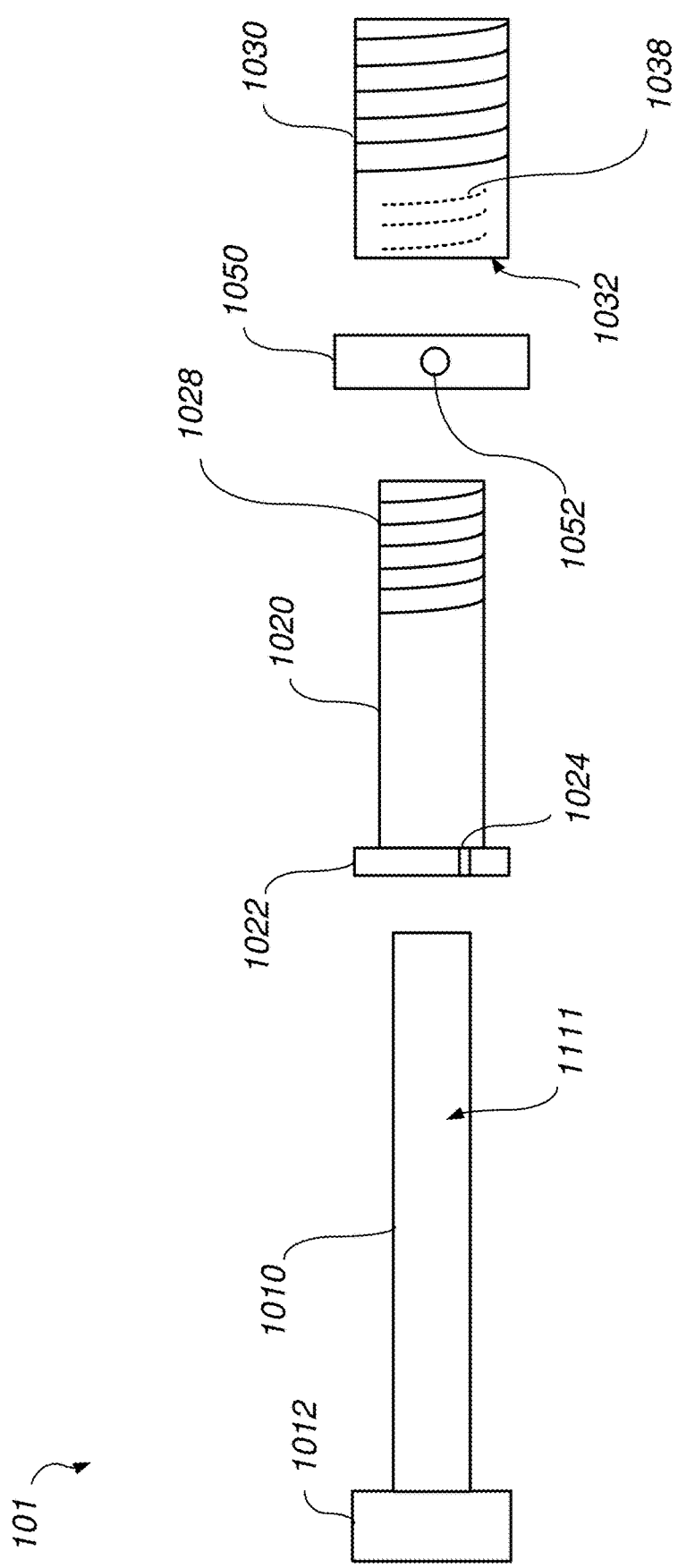
FIG. 11 is an exploded view of the user interface of FIG. 10.

Referring additionally to FIGS. 10 and 11, in various embodiments an illustrative user interface 101 for positioning electrodes includes an actuator shaft 1010, a primary actuator 1020, a secondary actuator 1030, and an actuator controller 1050. The actuator shaft 1010 provides a frame for operation of the user interface 101 and terminates in a mount 1012 that is couplable with a sheath actuator 604 as previously described with reference to FIGS. 6-9. The actuator shaft 1010 supports the primary actuator 1020, the secondary actuator 1030, and the actuator controller 1050. The actuator shaft 1010 defines a lumen through which the electrodes 207 and 211 (FIGS. 2-5) are conveyed.

In various embodiments, the primary actuator 1020 is slidably mounted on the actuator shaft 1010 and is coupled to the primary electrode 207 (FIGS. 2-5). The primary actuator 1020 includes a primary engagement interface 1022 that is configured to be engaged by the actuator controller 1050. The primary engagement interface 1022 of the primary actuator 1020 may include one or more engagement structures 1024. The one or more engagement structures 1024, which may include ridges, notches, or similar structures, are configured to positively engage a corresponding structure (not shown) on the actuator controller 1050. As described further below, the actuator controller 1050 may be moved in either direction along an axis 1001 of the user interface to engage the actuators 1020 and 1030 and to extend and retract the primary electrode 207 (not shown in FIGS. 10 and 11). For example, moving the actuator controller 1050 in a first direction 1003 may engage the actuator controller 1050 with the primary actuator 1020 and advance the primary actuator 1020 and the secondary actuator, as further described below. Moving the actuator controller 1050 in a second direction 1005 may engage the actuator controller 1050 with the secondary actuator 1030 to extend or retract the secondary electrode 211 or, when the actuator controller 1050 is engaged with the primary actuator 1020, may retract the primary electrode 207 and the secondary electrode 209, as also further described below.

In various embodiments, the one or more engagement structures 1024 may enable the actuator controller 1050 to be mechanically and/or frictionally engaged with the primary actuator 1020 to secure the actuator controller 1050 to the primary actuator 1020 as the actuator controller 1050 is used to slide the primary actuator 1020 along the axis 1001.

In various embodiments, the secondary actuator 1030 is threadably and rotatably mounted on the primary actuator 1020 and is mechanically coupled to the secondary electrode 211 (FIGS. 2-5). The secondary actuator 1030 includes a secondary engagement surface 1032 that, like the primary engagement interface 1022 of the primary actuator 1020, permits the secondary actuator 1030 to be positively engaged by the actuator controller 1050. As a result of the positive engagement, when the actuator controller 1050 is rotated, the secondary actuator 1030 also will be rotated. Referring to FIG. 11, the primary actuator 1020 includes a series of outward-facing threads 1028 that are threadably engaged by inward-facing threads 1038 (represented by dotted lines) inside the secondary actuator 1030. Engagement of the outward-facing threads 1028 of the primary actuator 1020 with the inward-facing threads 1038 of the secondary actuator 1030 facilitates the screwable movement of the secondary actuator 1030 relative to the primary actuator 1020 to advance and retract the secondary electrode 207, as further described below.

In various embodiments, the actuator controller 1050 is slidably mounted on the primary actuator 1020 where the actuator controller 1050 is selectively movable between the primary engagement interface 1022 of the primary actuator 1020 and the secondary engagement surface 1032 of the secondary actuator 1030. In various embodiments, the actuator controller 1050 may include a release mechanism 1052 that is used to selectively lock or unlock one or both of the primary actuator 1020 and the secondary actuator 1030 and/or to engage or disengage the actuator controller 1050 with the one or more engagement structures 1024 of the primary actuator 1020 and/or the engagement surface 1032 of the secondary actuator 1030.

As will be described further below, in various embodiments, the actuator controller 1050 thus serves as a single control surface that may be used to control both the primary actuator 1020 to manipulate the primary actuator 1020 and the secondary actuator 1030 without a user having to remove his or her hand from the actuator controller 1050 during manipulation of the electrodes 207 and 211. As will be further described below, because the secondary actuator 1030 is mounted on the primary actuator 1020, the actuator controller 1050 may be used to simultaneously move the primary actuator 1020 and the secondary actuator 1030 in concert to collectively move the primary electrode 207 and the secondary electrode 211 (FIGS. 2-5). In addition, the user can individually manipulate the secondary actuator 1030 and, thus, the secondary electrode 211 independently of the first electrode 207. In various embodiments, these manipulations are performable using only the single control surface provided by the actuator controller 1050.

Referring to FIGS. 12A-17B, the actuator controller 1050 is used to extend and retract the primary electrode 207 and the secondary electrode 211 to facilitate an electrosurgical procedure at a reference point 201 in a target region 202, such as ablation of tissue. For performing such a procedure, the user interface 101 may be coupled via the sheath actuator 604 to a bronchoscope 118 or similar insertion device 118 (not shown in FIGS. 12A-17B for the sake of visual simplicity) to control movements of the distal ends 209 and 213 of the primary electrode 207 and secondary electrode 211, respectively. In the example of FIGS. 12A-17B, it is assumed that the bronchoscope 118 or other insertion device has been used to convey the distal ends 209 and 213 of the primary electrode 207 and the secondary electrode 211, respectively, to the vicinity of the target region 202. It is also assumed that the sheath actuator 604 has been manipulated to position a distal end 105 of the sheath 103 directly adjacent to the target region 202.

Referring additionally to FIG. 12A, in various embodiments the user interface 101 is in a ready position with the primary actuator 1020 and the secondary actuator in retracted positions. Referring additionally to FIG. 12B, as a result, in various embodiments the distal ends 209 and 213 of the primary electrode 207 and the secondary electrode 211, respectively, are positioned within the distal end 105 of the sheath 103. In preparation for advancing the electrodes 207 and 211, the actuator controller 1050 is engaged with the primary engagement interface 1022 of the primary actuator 1020.

Referring additionally to FIG. 13A, in various embodiments the actuator controller 1050 is advanced a distance 1305. Because the actuator controller 1050 is engaged with the primary engagement interface 1022, moving the actuator controller 1050 through the distance 1305 advances the distal end 209 of the primary electrode 207 through the distance 1305. Also, because the secondary actuator 1030 is threadably mounted on the primary actuator 1020, advancing the primary actuator 1020 through the distance 1305 also advances the secondary actuator 1030 and the distal end 213 of the secondary electrode 211 through the distance 1305. As a result, the distal ends 209 and 213 of the primary electrode 207 and the secondary electrode 211, respectively, are both advanced into the target region 202 toward the reference point 201. In various embodiments, advancing the primary actuator 1020 with the actuator controller 1050 moves the secondary actuator 1030 in concert with the primary actuator 1020.

Figure 14A:
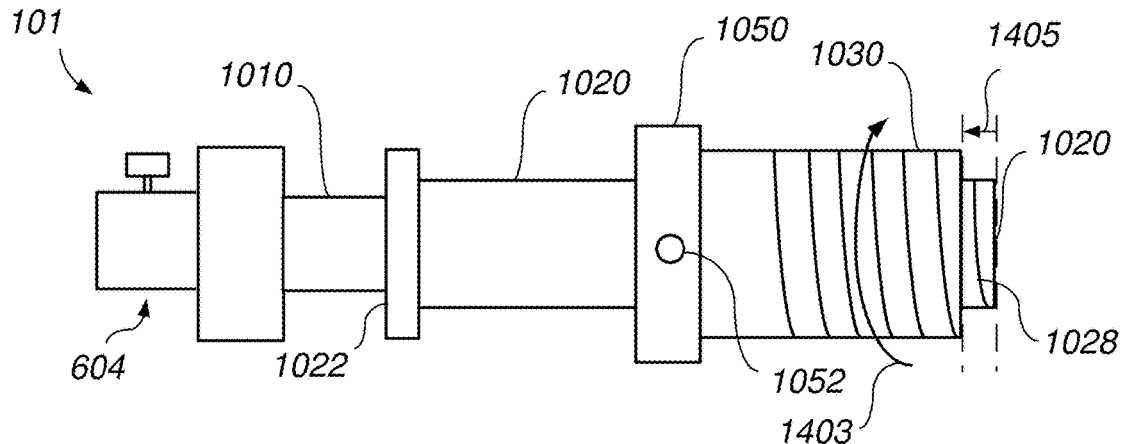

Referring additionally to FIG. 14A, in various embodiments after the primary electrode 207 and the secondary electrode 211 both have been extended into the target region 202, it is now desired to further extend the secondary electrode 211 into the target region 202 to position the distal ends 209 and 213 of the primary electrode 207 and the secondary electrode 211 across a distance before application of electric current to the tissue of interest. In various embodiments, this process is initiated by moving the actuator controller 1050 from the primary engagement interface 1022 of the primary actuator 1020 to the secondary engagement surface 1032 of the secondary actuator. In various embodiments, the release mechanism 1052 of the actuator controller 1050 may first be engaged to release the actuator controller 1050 from the primary engagement interface 1022 of the primary actuator 1020. In various embodiments, the release mechanism 1052 may be released by pressing the release mechanism 1052. In various embodiments, disengaging the actuator controller 1050 from the primary engagement surface 1022 of the primary actuator 1020 also may engage a locking mechanism (not shown) to hold the primary actuator 1020 in place relative to the actuator shaft 1010 and thereby hold the primary electrode 207 in place.

After withdrawing the actuator controller 1050 from the primary engagement surface 1022 of the primary actuator 1020, in various embodiments the actuator controller 1050 may be slidably moved across the primary actuator toward the secondary actuator 1030 and coupled with the secondary engagement surface 1032 of the secondary actuator 1030. The actuator controller 1050 then may be rotated in a direction 1403 to threadably advance the secondary actuator 1030 through a distance 1405 relative to the primary actuator 1020 to extend the distal end 213 of the secondary electrode 211.

Figure 14B:
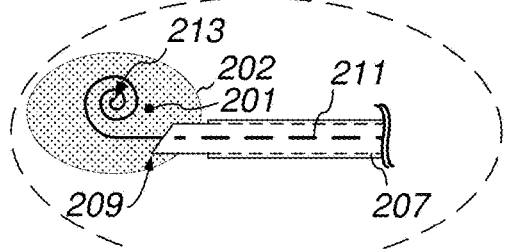

Referring additionally to FIG. 14B, in various embodiments extending the distal end 213 of the secondary electrode 211 results in the secondary electrode coiling into tissue of the target region 202 as previously described with reference to FIG. 5. With the distal end 213 of the secondary electrode 211 deployed at an opposite side of the reference point 201 from the distal end 209 of the primary electrode 207, an electric current may be applied between the distal ends 209 and 213 of the electrodes 207 and 211, respectively, to treat tissue at the reference point 201.

Figure 15A:
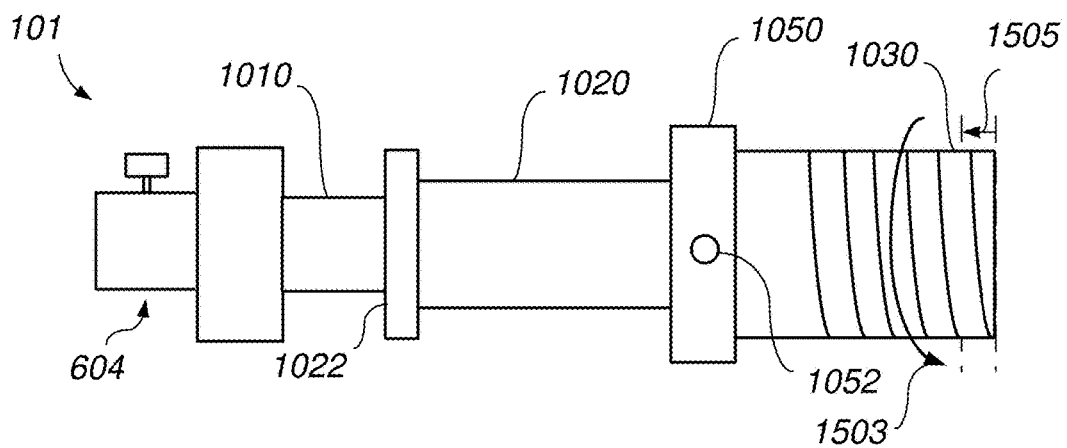
Figure 15B:
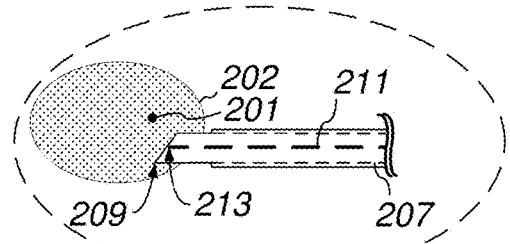

Referring additionally to FIGS. 15A and 15B, to retract the distal end 213 of the secondary electrode 211 back within the distal end 209 of the primary electrode 207, in various embodiments the actuator controller 1050 is rotated in an opposite direction 1503 to threadably retract the secondary actuator 1030 through a distance 1505.

Referring additionally to FIGS. 16A and 16B, to prepare for retraction of the primary electrode 207 and the secondary electrode 211 from the target region 202, in various embodiments the actuator controller 1050 is moved from the secondary engagement surface 1032 of the secondary actuator 1030 to the primary engagement interface 1022 of the primary actuator 1020. In various embodiments, the release mechanism 1052 of the actuator controller 1050 may be engaged to release the actuator controller 1050 from the secondary engagement surface 1032 of the secondary actuator 1030 and/or the actuator controller 1050 may be slid along the primary actuator 1020 until the actuator controller 1050 once again engages the primary engagement interface 1022 of the primary actuator 1020.

Referring additionally to FIGS. 17A and 17B, in various embodiments the primary electrode 207 and the secondary electrode 211 are withdrawn from the target region 202 by sliding the actuator controller 1050 rearward through a distance 1705. Because the secondary actuator 1030 is threadably mounted to the primary actuator 1020, sliding the primary actuator 1020 through the distance 1705 will simultaneously move the secondary electrode 211 through the same distance, thereby retracting the primary electrode 207 and the secondary electrode 211. After this operation, the distal end 213 of the secondary electrode 211 is retracted within the distal end 209 of the primary electrode 207, and both distal ends 209 and 213 are retracted within the distal end 105 of the sheath 103, thereby restoring the primary electrode 207 and the secondary electrode 211 to the starting position shown within the distal end 105 of the sheath 103 as described with reference to FIG. 12B.

Referring additionally to FIG. 18, an illustrative method 1800 of positioning electrodes for treatment is provided. The method 1800 starts at a block 1805. At a block 1810, a user interface, that includes a primary actuator operably coupled with a primary electrode and a secondary actuator operably coupled with a secondary electrode, is positioned to position distal ends of the primary electrode and the secondary electrode adjacent to a target region. At a block 1820, an actuator controller is moved in a first direction to engage the primary actuator. At a block 1830, the actuator controller is manipulated to advance the primary actuator to extend both the primary electrode and the secondary electrode. At a block 1840, the actuator controller is moved in a second direction to engage the secondary actuator. At a block 1850, the secondary actuator is manipulated to advance the secondary actuator to independently extend the secondary electrode beyond the primary electrode. The method ends at a block 1855, with the electrodes now positioned for the administration of treatment.

In some instances, one or more components may be referred to herein as "configured to," "configured by," "configurable to," "operable/operative to," "adapted/adaptable," "able to," "conformable/conformed to," etc. Those skilled in the art will recognize that such terms (for example "configured to") generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It will be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus comprising:
an actuator shaft defining a lumen through which a primary electrode and a secondary electrode are linearly movable along an axis of the lumen;
a primary actuator movably couplable with the actuator shaft and couplable with a primary electrode, the primary actuator being configured to extend and retract the primary electrode;
a secondary actuator movably couplable with the primary actuator and couplable with a secondary electrode, the secondary actuator being configured to extend and retract the secondary electrode; and
an actuator controller movably disposed around an elongate body of the primary actuator, the actuator controller configured to move along the elongate body in a first direction to engage with a shoulder portion of the primary actuator and motivate the primary actuator, the actuator controller being further configured to move along the elongate body in a second direction to engage a distal end of the secondary actuator and motivate the secondary actuator, the primary actuator and the secondary actuator being sequentially manipulatable responsive to manipulation of only the actuator controller.

2. The apparatus of claim 1, wherein the primary actuator is configured to be slidable relative to the actuator shaft to one of extend and retract the primary electrode.

3. The apparatus of claim 1, wherein the secondary actuator is movable in concert with the primary actuator to move the primary electrode and the secondary electrode in concert responsive to the actuator controller being engaged to motivate the primary actuator.

4. The apparatus of claim 1, wherein the secondary actuator is configured to be threadably coupled to the primary actuator, the secondary actuator being further configured to be threadably moved to extend and retract the secondary electrode without moving the primary electrode.

5. The apparatus of claim 1, wherein the actuator controller includes a sleeve configured to be slidable between the primary actuator and the secondary actuator.

6. The apparatus of claim 5, wherein the actuator controller includes a collar configured to alternately engage one of a primary actuator control surface and a secondary actuator control surface.

7. The apparatus of claim 6, wherein the primary actuator control surface includes a primary lock configured to hold the primary actuator in place relative to the actuator shaft until the primary lock is released, the primary lock being releasable by a user with the actuator controller engaging the primary actuator control surface.

8. The apparatus of Claim 7, wherein the actuator controller includes a lock release configured to be engageable by a user to release the primary lock.

9. The apparatus of claim 8, wherein the secondary actuator control surface includes a secondary lock configured to hold the secondary actuator in place relative to the primary actuator until the secondary lock is released, the secondary lock being releasable by a user with the actuator controller engaging the secondary actuator control surface.

10. A method comprising:
positioning a user interface, that includes a primary actuator operably coupled with a primary electrode and a secondary actuator operably coupled with a secondary electrode, to position distal ends of the primary electrode and the secondary electrode adjacent to a target region;
moving an actuator controller in a first direction to engage the primary actuator;
manipulating the actuator controller to advance the primary actuator to extend both the primary electrode and the secondary electrode;
moving the actuator controller in a second direction to engage the secondary actuator; and
manipulating the secondary actuator to advance the secondary actuator to independently extend the secondary electrode beyond the primary electrode.

11. The method of claim 10, further comprising:
sliding the actuator controller to advance the primary actuator to extend both the primary electrode and the secondary electrode; and
rotating the actuator controller to advance the secondary actuator to independently extend the secondary electrode beyond the primary electrode.

* * * * *